(12) United States Patent
Kwon et al.

(10) Patent No.: US 6,692,735 B1
(45) Date of Patent: Feb. 17, 2004

(54) VARIANT OF C6 β-CHEMOKINE LEUKOTACTIN-1(SHLKN-1) WITH ENHANCED BIOLOGICAL ACTIVITY

(75) Inventors: Byoung S. Kwon, Carmel, IN (US); Byung S. Youn, Seoul (KR); Soo-Il Chung, Kyounggi-do (KR); Doo-Hong Park, Seoul (KR); Seung Jae Baek, Kyounggi-do (KR); Eun-Kyoung Lee, Seoul (KR); Ju-Hyung Ahn, Kyounggi-do (KR); Kong-Ju Lee, Kyounggi-do (KR)

(73) Assignees: Korea Green Cross Corporation, Kyounggi-do (KR); Mogam Biotechnology Research Institute, Kyounggi-do (KR)

( * ) Notice: Subject to any disclaimer, the term of this patent is extended or adjusted under 35 U.S.C. 154(b) by 0 days.

(21) Appl. No.: 09/355,193

(22) PCT Filed: May 27, 1999

(86) PCT No.: PCT/KR99/00262

§ 371 (c)(1),
(2), (4) Date: Jul. 21, 1999

(87) PCT Pub. No.: WO00/73456

PCT Pub. Date: Dec. 7, 2000

(51) Int. Cl.[7] .......................... C07K 14/52; C12N 5/10; C12N 15/19; C12N 15/63
(52) U.S. Cl. ..................... 424/85.1; 530/324; 435/69.5; 435/71.1; 435/71.2; 435/471; 435/320.1; 435/252.3; 435/255.5
(58) Field of Search ....................... 514/4, 8; 424/85.1; 435/69.5, 71.1, 71.2, 252.3, 254.11, 255.5, 320.1, 471, 325; 530/324

(56) References Cited

PUBLICATIONS

Youn BS. et al. 1997, J Immumol. vol. 159, pp. 5201–5205. Molecular cloning of lekotactin–1: Anovel human beta–chemokine, a chemoattractant for neutrophils, monocytes, and lymphocytes, and a potent agonist at CC chemokine receptors 1 and 3.*

Macphee et al. 1998, J Immunol. vol. 161, pp. 6273–6279. Identificationof atruncated form of the CC chemokine CKbeta demonstrating greatly enahnced bioloigcal activity.*

Hromas et al. 2000. Blood. vol. 95, pp. 1506–1508. The exodus subfamily of CC chemokines inhibits the proliferation of chronic myelogenous leukemia progenitors.*

Virelizier JL. 1999. Dev Biol Stand. vol. 97, pp. 105–109. Blocking of HIV co–recepotr by chemokines.*

J. Fernando Bazan et al., A new class of membrane–bound chemokine with a CX 3C motif, Nature, 385(13):640–644, 1997.

Byung–S. Youn et al., A novel chemokine, macrosphage inflammatory protein–related protein–2, inhibits colony formation of bone marrow myeloid progentorors, J. Immunol., 155:26661–2667, 1995.

* cited by examiner

Primary Examiner—Prema Mertz
(74) Attorney, Agent, or Firm—Darby & Darby

(57) ABSTRACT

The present invention relates to a variant of Lkn-1(shLkn-1) with enhanced biological activity, which is a truncated form of Lkn-1, a process for preparing a recombinant shLkn-1 by employing expression vector therefor and pharmaceutical application of the said protein. shLkn-1 is generated by missing 26 amino acid residues from the amino terminus of Lkn-1 to contain 66 amino acids. Recombinant shLkn-1 inhibits colony formation and cell proliferation in vivo, which suggests that it can be used as a potential drug for the antibody production, the treatment during HIV-1 infection, the protection of bone marrow stem cells during chemotherapy or radiotherapy, and the inhibition of leukemia.

13 Claims, 5 Drawing Sheets

ShLkn-1
(10ng/ml)

Lkn-1
(100ng/ml)

Lkn-1    SM    shLkn-1

1   2   3   4

VARIANT OF C6 β-CHEMOKINE LEUKOTACTIN-1(SHLKN-1) WITH ENHANCED BIOLOGICAL ACTIVITY

BACKGROUND OF THE INVENTION

1. Field of the Invention

The present invention relates to a variant of C6β-chemokine (shLkn-1) with enhanced biological activity, more specifically, to a variant of Lkn-1 which belongs to C6 β-chemokine, a process for preparing a recombinant shLkn-1 by employing expression vector therefor, and pharmaceutical application of the said protein.

2. Description of the Prior Art

Chemokines, a family of small cytokines consisting of basic proteins of low molecular weight, have four cysteine residues commonly, which are classified into four subfamilies of CXC(α), CC(β), C(γ) and $CX_3C$ depending on the position of the first and the second cysteines, i.e., whether they lie adjacent or an amino acid intervenes between the two cysteines (see: Baggiolini, M. and Dahinden, C. A., Immunol. Today, 15:127(1994); Kelner, S. G. et al., Science, 266:1395(1994); Bazan, J. F. et al., Nature, 385:640(1997)). Genes of chemokine subfamilies locate on a same chromosome in a cluster, for example, α-chemokine genes locate on the human chromosome 4q12–21 and β-chemokine genes exist on the human chromosome 17q11–32 and the mouse chromosome 11.

Some chemokines have biological activities such as HIV-inhibitory action, immunoregulatory action, leukocyte migration or inhibitory action against division of hematopoietic stem cells (see: Cocchi, F. et al., Science, 270:1811 (1995); Wolpe, S. D. et al., J. Exp. Med., 167:570(1988); Graham, G. J. et al., Nature, 344:442(1990);

Broxmeyer, H. E. et al., Blood, 76:1110(1990); Youn, B.-S. et al., J. Immunol., 155:2661–2667(1995)).

Also, chemokines bind to transmembrane domain of G protein-coupled receptors to activate leukocytes and some of the receptors are also used as coreceptors in the course of HIV-1 infection(see: Oh, K. -O. et al., J. Immunol., 147:2978(1991); Alkabatih, G. et al., Science, 272:1955 (1996)). For example, among 8 subtypes of β-chemokine (CC chemokine) receptor, i.e., CCR1, CCR2, CCR3, CCR4, CCR5, CCR6, CCR7 and CCR8, four subtypes of CCR4, CCR6, CCR7 and CCR8 show a high affinity to one substance while CCR1, CCR2, CCR3 and CCR5 have a binding affinity to various chemokines.

So far, more than nine chemokines belonging to β-chemokine subfamily have been found(see: Wilson, S. D. et al., J. Exp. Med., 171:1301(1990); Modi, W. S. et al., Hum. Genet., 84:185(1990)). Among them, a murine MRP-1 ("mMRP-1", MIP(macrophage inflammatory protein)-related protein-1 or C10) (see: Orlofsky, A. et al., Cell Regul., 2:403(1991)), a murine MRP-2("mMRP-2") (see: Youn, B. -S. et al., J. Immunol., 155:2661(1995)), and a human Lkn-1(Leukotactin-1) (see: Youn, B. -S. et al., J. Immunol., 159:5201 (1997)) are distinguished from the rest of -chemokines in the senses that they have two extra cysteine residues, thereby forming the third disulfide bond, and their N-terminal regions are very long. Based on the findings, they are classified into C6 β-chemokines.

Meanwhile, it was observed that expression of Lkn-1 from recombinant yeast cells such as *Pichia pastoris*("*P. pastoris*") results in a recombinant protein with a smaller size than expected for intact Lkn-1 of 92 amino acid residues. The N-terminal amino acid sequence of this smaller form is consistent with that of truncation form Lkn-1 in which 26 amino acids of N-terminus are deleted. Similar truncation of N-terminus has been reported for MPIF-1 (Myeloid Progenitor Inhibitory Factor-1) which is closely related to Lkn-1 in terms of the presence of the extra pair of cysteine residues and the unusually long N-terminus(see: Macphee C. H. et al., J. Immunol., 161:6273(1998)). In this connection, it was suggested that the truncation is correlated with the increase of the biological activity.

Under the circumstances, there are strong reasons for exploring and developing the truncated variant of Lkn-1, since the shorter version may have enhanced biological activity as with MPIF-1 and advantages in mass production. When compared with the native molecule, Lkn-1, the truncated variant of Lkn-1 may have improved potential biological activity as a drug for the treatment of HIV-1 infection or for the protection of bone marrow stem cells during chemotherapy or radiotherapy.

SUMMARY OF THE INVENTION

The present inventors isolated a truncated form of Lkn-1 from the culture media of *P. pastoris* harboring the gene for Lkn-1, and discovered that the truncated Lkn-1 protein indeed has enhanced biological activity as compared with the native Lkn-1. Further, they constructed a cDNA for the truncated form, expressed the said mutant cDNA in a recombinant *P. pastoris*, and showed the expressed recombinant protein inhibits colony formation and proliferation of myeloid stem cell and progenitor cell in vivo. Hereinafter, the said truncated form protein and the recombinant protein thereof are referred to as "shLkn-1"(short version of human leukotactin-1) and "recombinant shLkn-1", respectively.

The first object of the invention is, therefore, to provide shLkn-1 which has an enhanced biological activity as compared with the intact Lkn-1.

The second object of the invention is to provide an expression vector comprising a cDNA for the said shLkn-1 and a recombinant microorganism transformed with the vector.

The third object of the invention is to provide a process for preparing a recombinant shLkn-1 from the said microorganism.

The fourth object of the invention is to provide a pharmaceutical composition for the antibody production, the treatment during HIV-1 infection, the protection of bone marrow stem cells during chemotherapy or radiotherapy, the inhibition of leukemia.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

The present inventors have isolated Lkn-1 cDNA from the cDNA library prepared from a human monocytic THP-1 cell line activated by interleukin-4(IL-4). The Lkn-1 cDNA thus cloned was inserted into a vector pPIC9 to construct an expression vector for Lkn-1, pPM2, and introduced into *P. pastoris* to express the recombinant Lkn-1.

The recombinant Lkn-1 was expressed and secreted from the host cells into growth media upon induction with methanol. Analysis by SDS-polyacrylamide gel electrophoresis revealed that the size of the recombinant protein was smaller than that expected for mature Lkn-1. The apparently truncated form was purified with two steps of ion exchange column chromatography by using SP-Sepharose column. N-terminal sequencing has proven that the said protein is generated by the truncation of the N-terminal fragment of 26 amino acid residues from the mature Lkn-1 and hence the truncated form was designated as shLkn-1. The recombinant shLkn-1 was a stronger agonist at CCR1 than recombinant Lkn-1.

To construct an expression system for stable and highly efficient expression of recombinant shLkn-1 in *P. pastoris*, the present inventors first generated a DNA fragment encoding shLkn-1 by the polymerase chain reaction(PCR) and then inserted the DNA fragment into the expression vector pPIC9. The expression vector pPM2-HF thus constructed was transformed into a host cell of *P. pastoris* and a recombinant strain capable of high level expression of shLkn-1 was selected. Recombinant shLkn-1 was expressed and secreted from host cells into culture media upon induction with methanol.

The recombinant shLkn-1 purified from the culture media is a stronger agonist of CCR1 than recombinant Lkn-1 and inhibits colony formation, and cell proliferation of granulocyte-macrophage progenitors in vivo.

The recombinant shLkn-1 of the invention showing the characteristics mentioned above can be used for the antibody production, the treatment during HIV-1 infection, the protection of bone marrow stem cells during chemotherapy or radiotherapy, and the inhibition of leukemia.

The present invention is further illustrated in the following examples, which should not be taken to limit the scope of the invention.

EXAMPLE 1

Identification of a Truncated Form of Lkn-1

Figure 1:
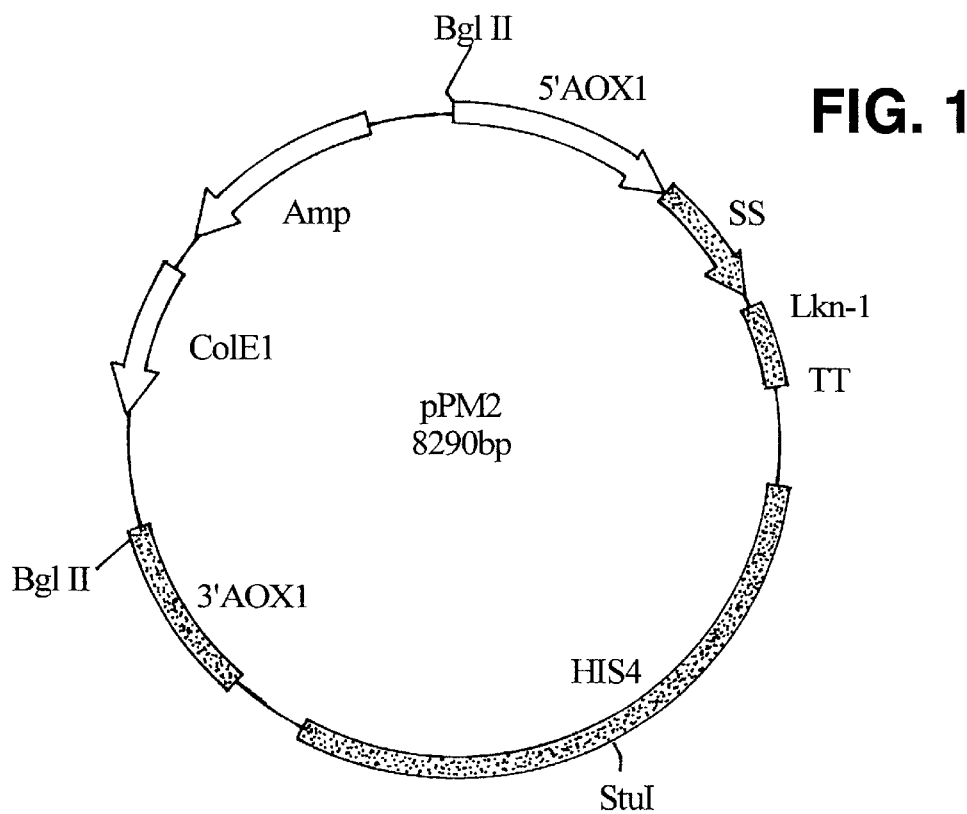
FIG. 1 is a schematic representation of an expression vector pPM2 which is used to prepare recombinant Lkn-1 in *P. pastoris*.

In order to express Lkn-1 in *P. pastoris*, an expression vector pPM2 depicted in FIG. 1 was linearized with a restriction enzyme StuI and used for transformation of *P. pastoris* GS115 host cells by the electroporation method. Transformants of *P. pastoris* on selective agar plate were inoculated in 50 ml Minimal Dextrose (MD) media and grown at 30° C. overnight. The seed culture was centrifuged and the harvested cells were inoculated into Minimal Methanol(MM) media. The cells were grown at 30° C. with vigorous shaking to an $OD_{600}$ of 1 and the expression and secretion of recombinant Lkn-1 from *P. pastoris* were induced by addition of 100% methanol to the culture media to a final concentration of 0.5% every 24 hours. By SDS-polyacrylamide gel electrophoresis and calcium mobilization assay with HEK293 cell line which was transfected with CCR1 receptor, a recombinant clone *P. pastoris*/pPM2 with the highest expression of Lkn-1 was selected.

Figure 2:
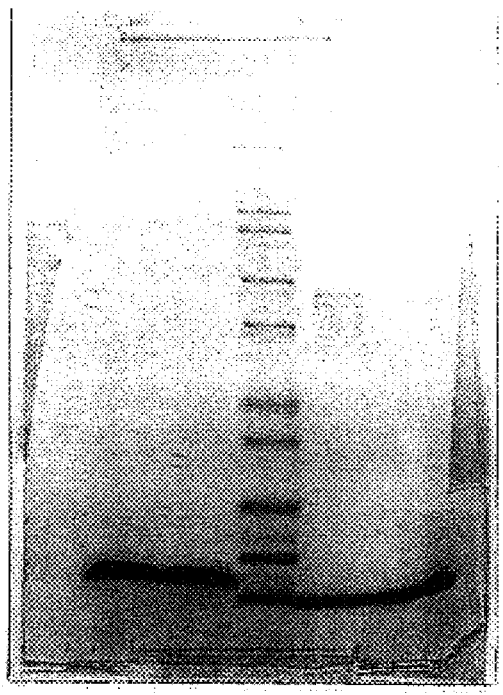
FIG. 2 is a photographshowing a truncated form of Lkn-1 produced from recombinant *P. pastoris* of SDS-polyacrylamide gel.

High level of recombinant Lkn-1 expression was achieved by high density cell culture of recombinant *P. pastoris*/pPM2 using a BioFloIII fermenter(New Brunswick Scientific, U.S.A.) and a DO-stat control strategy. SDS-polyacrylamide gel electrophoresis of the culture broth from the fermentation revealed that the mature form of Lkn-1 with 92 amino acid residues appeared to be converted to a form with a smaller size as shown in FIG. 2. In FIG. 2, Lkn-1, SM and shLkn-1 represent mature form of Lkn-1, molecular weight size marker and smaller size Lkn-1, respectively.

The said recombinant protein with the apparently smaller size was purified from the culture broth by consecutive ion exchange column chromatographic steps by using SP-Sepharose column. The culture broth was diluted 3-fold with 20 mM sodium phosphate buffer, pH 7.4 and applied to a SP-Sepharose column. After washing the column with the same buffer containing 0. 1M NaCl, the truncated form of Lkn-1 was eluted from the column with the sodium phosphate buffer, pH 7.4, containing 0.3M NaCl. The pool of the fractions containing the said protein as analyzed by SDS-polyacrylamide gel electrophoresis was diluted 4-fold with 20 mM sodium phosphate, pH7.4, and applied to a SP-Sepharose column. Unbound portion was washed away from the column with 20 mM sodium phosphate, pH 7.4, containing 0.1M NaCl. The truncated form of Lkn-1 was eluted from the column using a linear gradient of NaCl from 0.25 to 0.3M in the same buffer. The purity of the said protein was over 95% as determined by analytical reversed-phase HPLC.

The first amino acid of the purified recombinant protein was histidine as determined by Edman degradation amino acid sequencing, confirming a truncation of 26 amino acid residues from the amino terminus of Lkn-1. The molecular weight of the said protein measured by mass spectrometric analysis was also consistent with the truncation of 26 residues from the mature Lkn-1. Hence the truncated Lkn-1 was named shLkn-1(short version of human leukotactin-1).

Figure 3A:
FIG. 3(A) is a graph showing fluorescence emission measured in a HEK293 cell line expressing CCR1 which is stimulated by recombinant shLkn-1.
Figure 3B:
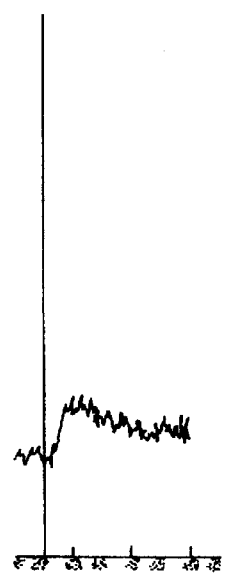
FIG. 3(B) is a graph showing fluorescence emission measured in a HEK293 cell line expressing CCR1 which is stimulated by recombinant Lkn-1.

Biological activity of shLkn-1 was compared to that of mature Lkn-1 by calcium mobilization assay using HEK293 cell line expressing CCR1. Cells were harvested by trypsinization, washed twice with HBSS(10 mM HEPES(pH 7.4), 0.8 mM $MgCl_2$, and 1.8mM $CaCl_2$) and loaded in HBSS containing 2$\mu$M FURA-2/AM for 45 min at 37° C. in the dark. Cells were washed twice in HBSS and resuspended at $1\times10^6$/ml in HBSS(pH 7.4). 2 ml of cell suspension was placed in a stirred, water-jacketed cuvette at 37° C. and excited at 340nm. Fluorescence emission was monitored at 510nm before and after addition of agonists, and the data were presented as the relative fluorescence level. As shown in FIGS. 3(A) and 3(B), the amplitude of fluorescence change evoked with 10ng/ml of shLkn-1 was even greater than that evoked with 100ng/ml of mature Lkn-1, indicating that shLkn-1 was far more active than Lkn-1 in stimulating intracellular calcium mobilization through CCR1.

EXAMPLE 2

Construction of an Expression Vector for shLkn-1, pPM2-HF

Figure 4:
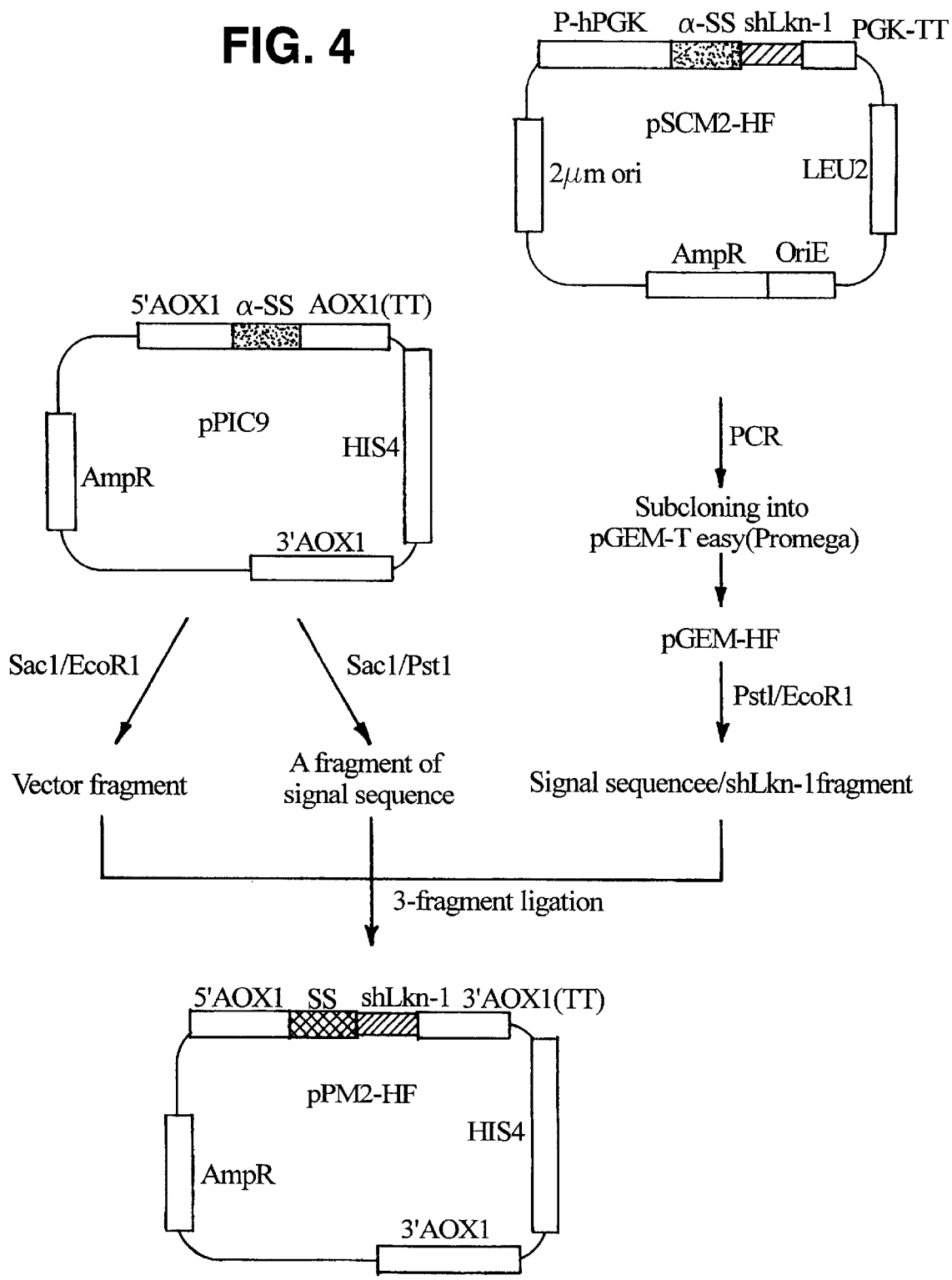
FIG. 4 depicts the construction strategy of an expression plasmid pPM2-HF which is used to prepare shLkn-1 in *P. pastoris*.

The expression vector pPM2-HF for the production of shLkn-1 in *P. pastoris* was constructed in accordance with the strategy shown in FIG. 4. A plasmid for the expression of shLkn-1 in a yeast strain *Saccharomyces cerevisiae* was constructed and designated as pSCM2-HF whose map is also shown in FIG. 4. A DNA fragment corresponding to a fusion protein of the secretion signal sequence of yeast α-factor and shLkn-1 was amplified by polymerase chain reaction using the pSCM2-HF plasmid as a template, a set of forward and reverse primers, and Ex Taq DNA polymerase(TaKaRa, Japan):

forward primer:
5'-GCGCGCTCATGAGATTTCCTTCAATTTTTAC-3'
(SEQ ID NO:3)
reverse primer:
5'-GCGCGCGAATTCCTATTATATTGAGTAGGGCT-TCAG-3'
(SEQ ID NO:4)

The DNA fragment thus amplified was ligated into PGEM-T Easy vector(Promega, U.S.A.) to make the pGEM-HF plasmid. In order to construct the pPM2-HF plasmid, a three-fragment ligation was carried out. The pGEM-HF plasmid was digested with PstI/EcoRI and a fragment thus generated and containing the shLkn-1 coding region fused to a part of the signal sequence was isolated. The plasmid pPIC9(Invitrogen, U.S.A.) was digested separately with either SacI/EcoRI or SacI/PstI from which a fragment of 7009 base pairs and a fragment of 767 base pairs were isolated, respectively. The recombinant plasmid thus constructed was confirmed by restriction digestion mapping and DNA sequencing and designated as pPM2-HF. The nucleotide sequence of shLkn-1 coding region(SEQ. ID NO: 1) and the amino acid sequence deduced from the nucleotide sequence(SEQ. ID NO: 2) are provided in the Sequence Listing. The expression vector pPM2-HF was linearized with a restriction enzyme StuI and introduced into *P. pastoris*. The recombinant plasmid pPM2-HF permits expression and secretion of recombinant shLkn-1 from *P. pastoris*. A transformant capable of high level expression of shLkn-1 was selected as described in Example 1. The transformant thus prepared was designated as GS115:pPM2-HF and deposited with the Korean Culture Center of Microorganisms(KCCM, 361-221, Hongje-1-dong, a Seodaemun-gu, Seoul 120-091, Republic of Korea), an international depository authority as accession No. KCCM-10159, on May 13, 1999.

EXAMPLE 3

Expression and Purification of Recombinant shLkn-1 from *P. pastoris*

Figure 5:
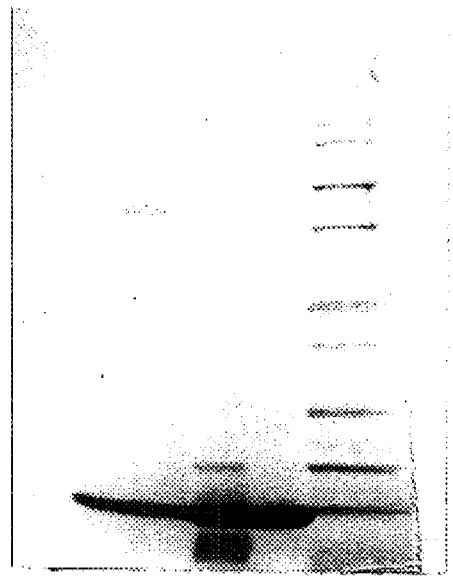
FIG. 5 is a photograph of SDS-polyacrylamide gel showing recombinant shLkn-1 purified from *P. pastoris*.

Expression in *P. pastoris* and purification from the culture media of recombinant shLkn-1 were carried out analogously as in Example 1. FIG. 5 shows the purified recombinant shLkn-1 analysed by SDS-polyacrylamide gel electrophoresis, where lane 1 is fermenatation culture broth; lane 2 is 1st SP-Sepharose pool; lane 3 is 2nd SP-Sepharose pool; and, lane 4 is molecular weight size marker.

EXAMPLE 4

Analysis of Calcium Flux in HEK293 Cell Line Expressing CCR1 Chemokine Receptor

Figure 6:
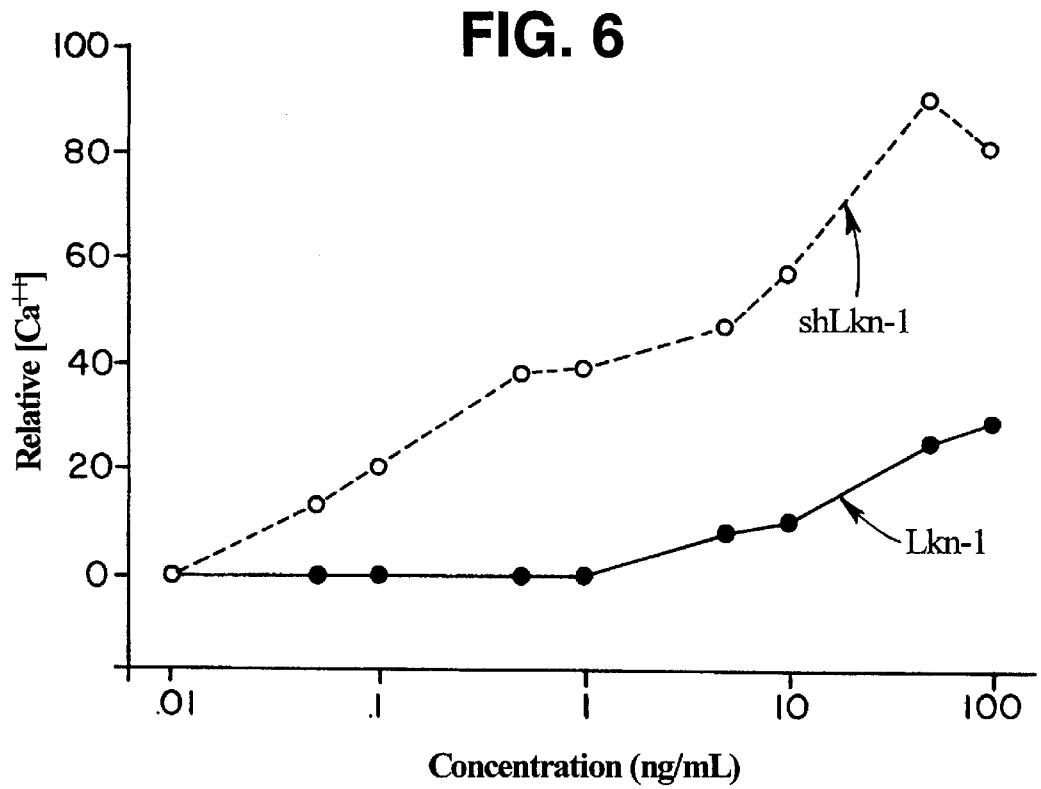
FIG. 6 is a graph showing peak amplitude of calcium responses depending on concentrations of recombinant shLkn-1 and Lkn-1.

It was shown that Lkn-1 can activate a cell line expressing CCR1 or CCR3 chemokine receptors. In order to compare biological activities of shLkn-1 and mature Lkn-1, dose dependencies of calcium mobilization with varied concentrations of either protein were carried out using HEK293 cell line expressing CCR1 chemokine receptor, which was analyzed in a similar manner as in Example 1. As shown in FIG. 6, the relative calcium responses depending on concentrations of shLkn-1(-○-) and Lkn-1(-●-) showed that the recombinant shLkn-1 is a stronger agonist against CCR1 than recombinant Lkn-1.

EXAMPLE 5

Inhibition of Proliferation of Myeloid Cells by the Recombinant shLkn-1 in vivo

Figure 7A:
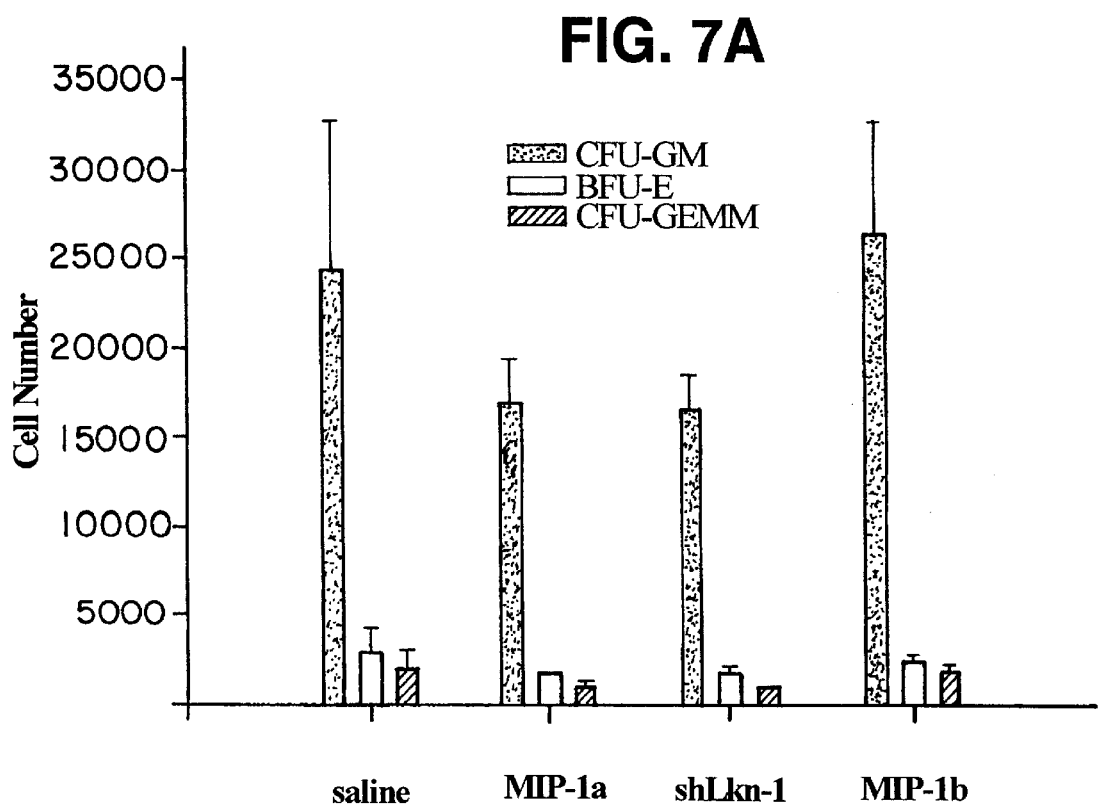
FIG. 7(A) is a graph showing effect of Lkn-1 on the colony formation of myeloid stem/progenitor cells in bone marrow.
Figure 7B:
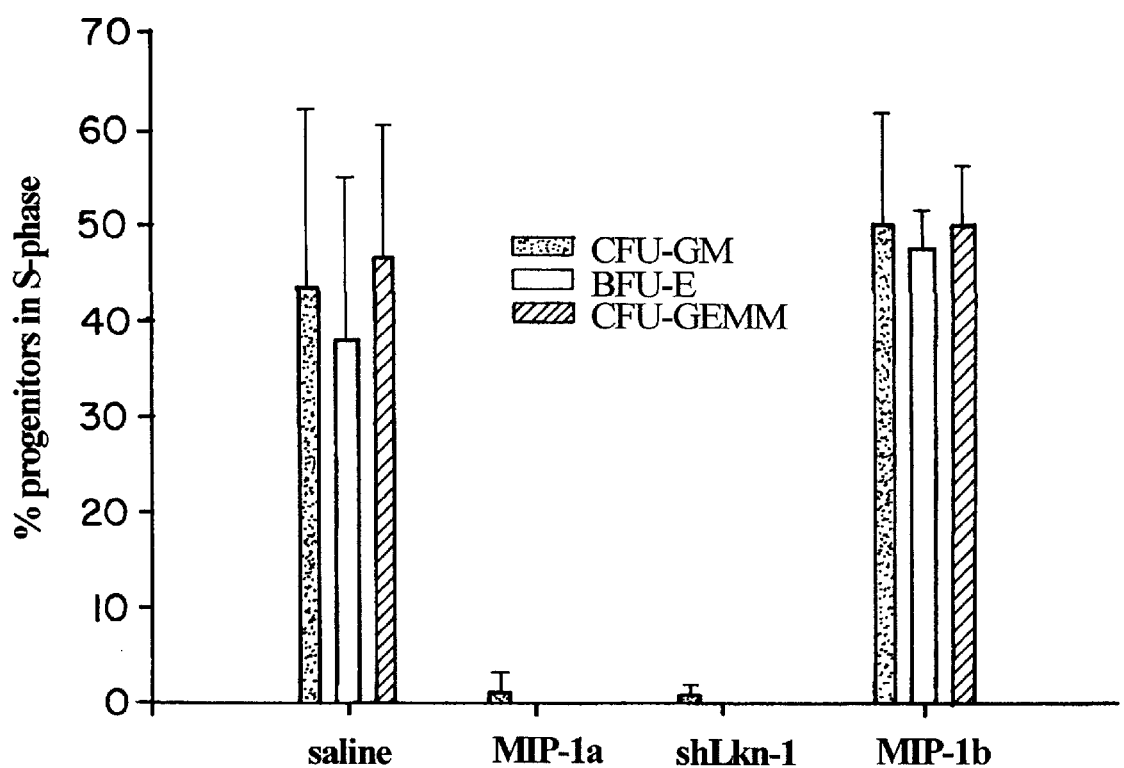
FIG. 7(B) is a graph showing effect of Lkn-1 on the proliferation rate of myeloid stem/progenitor cells in bone marrow.

The biological activity of shLkn-1 was evaluated in vivo. That is, the purified shLkn-1 was intravenously injected into C3H/HeJ mice and absolute numbers of granulocyte macrophage("CFU-GM"), erythroid("BFU-E") and multi-potential progenitor cells("CFU-GEMM") and their proliferation rates were determined in bone marrow as follows: C3H/HeJ mice were injected through the tail vein with either 0.1 ml of sterile pyrogen-free saline or 10 $\mu$g of purified shLkn-1 diluted in sterile pyrogen-free saline. At the same time, separate group of C3H/HeJ mice were injected with either 10 $\mu$g of MIP-1α (Macrophage Inflammatory Protein-1α) or 10 $\mu$g of MIP-1β (Macrophage Inflammatory Protein-1β) as a positive and negative control, respectively, for the myelosuppressive activity. After 24 h from the injection, myeloid cells of low density were prepared from bone marrow of femur of the mice. Then, CFU-GM was plated on 0.3% agar culture medium, and stimulated by 10% PWM mouse spleen cell-conditioned medium. Similarly, BFU-E and CFU-GEMM were plated on 0.9% methylcellulose culture medium, respectively, and stimulated by 1 unit of rhEPO, 0.1 mmole/hemin and 1% PWM mouse spleen cell-conditioned medium. In this connection, the bone marrow cells were plated at a concentration of $7.5 \times 10^4$ cells/ml. After the stimulation, the cells were cultured in a BNP-210 incubator(Tabai ESPEC Corp., U.S.A.) under an environment of 5% $CO_2$ and 5% $O_2$, and number of colonies was counted after 5 to 7 days of incubation(see: FIG. 7(A)). On the other hand, proliferation rates, i.e., cycling rates of CFU-GM, BFU-E and CFU-GEMM were determined as percentage of the cells in S-phase of cell cycle by measuring the proportion of progenitors in DNA synthesis(i.e., S-phase of cell cycle) by the aid of tritiated thymidine(50 $\mu$Ci/ml, 20Ci/mmol) killing technique, which is based on in vitro calculation of reduction in the number of colonies formed after pulse exposure of cells to hot tritiated thymidine for 20 min as compared with a comparable amount of cold thymidine(see: FIG. 7(B)). FIGS. 7 (A) and 7 (B) revealed that shLkn-1 rapidly decreased numbers of colonies by myeloid stem/progenitor cells and their proliferation rate, i.e., cell cycling rate in the bone marrow. The overall cell cycling rate was completely abolished by shLkn-1. On the other hand, the nucleated cellularity in bone marrow, spleen and blood were assessed, and found to be not significantly affected as compared with control.

These effects of shLkn-1 on proliferation of stem/progenitor cells strongly suggested that: shLkn-1 has a potential clinical use in protecting normal hematopoietic cells from cytotoxic anti-cancer drugs or radiation.

Acute Toxicity Test

Acute toxicity was examined using 6-week-old SD(Sprague-Dawley) rats. 1 ml of PBS(phosphate buffered saline) containing shLkn-1 (dose: 60 mg/kg) was intravenously injected into 10 rats and the rats were observed. As a result, all tested animals were survived, and there was no striking symptom or other toxic effect. shLkn-1 did not elicit any toxic effect when injected to rats within the range of 60 mg/kg, thus proved to be safe material for parenteral administration.

shLkn-1 may be used as an active ingredient of a parmaceutical composition for the antibody production, the treatment during HIV-1 infection, the protection of bone marrow stem cells during chemotherapy or radiotherapy, and the inhibition of leukemia, in a free form or in a formulation with pharmaceutically acceptable carrier for oral, intravenous or subcutaneous administration. Orally, the pharmaceutical composition can be formulated in the form of tablets, capsules, granules, powders and the like. In addition, the pharmaceutical composition may comprise additives such as surfactants, paraplasms, coloring agents, stabilizers, buffers, suspensions, isotonics or other conventional additives, and inorganic or organic carriers to formulate solid, semi-solid or liquid-type preparation.

The effective dose of pharmaceutical composition provided by the present invention is variable depending on the way of treatment, administration or the type of disease, the age of patient and the duration of administration. In the administration via vein and muscle, the effective dose ranges from 0.1 to 5 mg/kg, and in the case of the oral administration, the range falls into 1.0 to 30 mg/kg.

As clearly illustrated and demonstrated as above, the present invention provides a variant of Lkn-1 with enhanced biological activity as compared to the parent molecule. Amino acid sequencing revealed that: the variant is a truncated form of Lkn-1 which is generated by missing 26 amino acid residues from the amino terminus of Lkn-1; hence, shLkn-1 contains 66 amino acids whose molecular weight estimates about 7,200 daltons. Recombinant shLkn-1 which is expressed, secreted from *P. pastoris* and purified to near homogeneity is shown to be more active than mature Lkn-1. Recombinant shLkn-1 inhibits colony formation and cell proliferation in vivo, which suggests that it can be used as a potential drug for the antibody production, the treatment during HIV-1 infection, the protection of bone marrow stem cells during chemotherapy or radiotherapy, the inhibition of leukemia. Further, it was also determined that the recombinant shLkn-1 may provide simplicity to the production and storage of the said protein as compared with the parent molecule Lkn-1.

What is claimed is:

1. A truncated variant of C6 β-chemokine leukotactin-1 polypeptide consisting of the amino acid sequence of SEQ ID NO:2.

2. A cDNA encoding the truncated C6β-chemokine leukotactin-1 polypeptide variant of claim 1.

3. An expression vector comprising the cDNA of claim 2.

4. A recombinant microorganism transformed with the expression vector of claim 3.

5. A process for preparing a recombinant truncated C6β-chemokine leukotactin-1, wherein said process comprises the steps of culturing the recombinant microorganism of claim 4 and obtaining the truncated C6β-chemokine leukotactin-1 from the culture.

6. The process for preparing the recombinant truncated C6β-chemokine leukotactin-1 polypeptide of claim 5, wherein the recombinant microorganism is *Pichia pastoris* strain GS115:pPM2-HF.

7. A recombinant truncated C6β-chemokine leukotactin-1 prepared by the process of claim 5.

8. A pharmaceutical composition which comprises the recombinant truncated C6β-chemokine leukotactin-1 of claim 7 and a pharmaceutically acceptable carrier.

9. The pharmaceutical composition of claim 8 which is effective for an antibody production.

10. The cDNA of claim 2 consisting of a nucleotide sequence corresponding to SEQ ID NO: 1.

11. The expression vector of claim 3, wherein said vector is pPM2-HF.

12. The recombinant microorganism of claim 4, wherein the microorganism is *Pichia pastoris* strain GS115:pPM2-HF (KCCM-10159).

13. The pharmaceutical composition of claim 8, wherein said pharmaceutically acceptable carrier is selected from the group consisting of surfactants, coloring agents, stabilizers, buffers, and inorganic or organic carriers.

* * * * *

SEQUENCE LISTING

<160> NUMBER OF SEQ ID NOS: 4

<210> SEQ ID NO 1
<211> LENGTH: 201
<212> TYPE: DNA
<213> ORGANISM: Homo sapiens

<400> SEQUENCE: 1

```
cactttgctg ctgactgctg cacctcctac atctcacaaa gcatcccgtg ttcactcatg      60
aaaagttatt ttgaaacgag cagcgagtgc tccaagccag gtgtcatatt cctcaccaag     120 aagggcggc aagtctgtgc caaacccagt ggtccgggag ttcaggattg catgaaaaag     180
ctgaagccct actcaatata a                                                201
```

<210> SEQ ID NO 2
<211> LENGTH: 66
<212> TYPE: PRT
<213> ORGANISM: Homo sapiens

<400> SEQUENCE: 2

```
His Phe Ala Ala Asp Cys Cys Thr Ser Tyr Ile Ser Gln Ser Ile Pro
 1               5                  10                  15

Cys Ser Leu Met Lys Ser Tyr Phe Glu Thr Ser Ser Glu Cys Ser Lys
            20                  25                  30

Pro Gly Val Ile Phe Leu Thr Lys Lys Gly Arg Gln Val Cys Ala Lys
        35                  40                  45

Pro Ser Gly Pro Gly Val Gln Asp Cys Met Lys Lys Leu Lys Pro Tyr
    50                  55                  60

Ser Ile
 65
```

-continued

```
<210> SEQ ID NO 3
<211> LENGTH: 31
<212> TYPE: DNA
<213> ORGANISM: Artificial Sequence
<220> FEATURE:
<223> OTHER INFORMATION: forward primer

<400> SEQUENCE: 3
gcgcgctcat gagatttcct tcaattttta c                                    31

<210> SEQ ID NO 4
<211> LENGTH: 36
<212> TYPE: DNA
<213> ORGANISM: Artificial Sequence
<220> FEATURE:
<223> OTHER INFORMATION: reverse primer

<400> SEQUENCE: 4
gcgcgcgaat tcctattata ttgagtaggg cttcag                               36
```